United States Patent [19]

Centner

[11] 4,161,353
[45] Jul. 17, 1979

[54] SECONDARY IMAGE REPRODUCTION DEVICE

[76] Inventor: Herman Centner, 8730 SW. 21 Terr., Miami, Fla. 33165

[21] Appl. No.: 818,054

[22] Filed: Jul. 22, 1977

[51] Int. Cl.² .................. A61B 3/02; G03B 21/26; G03B 21/28

[52] U.S. Cl. .................................... 351/30; 353/34; 353/37

[58] Field of Search ............... 351/30, 36, 31; 353/21, 353/24, 37

[56] References Cited

U.S. PATENT DOCUMENTS

| | | | |
|---|---|---|---|
| 3,768,891 | 10/1973 | Centner | 351/30 |
| 3,947,098 | 3/1976 | Paget | 351/30 |

Primary Examiner—John K. Corbin
Assistant Examiner—Rodney B. Bovernick

[57] ABSTRACT

A device to attach to an optical projector having a beam opening for passage of a beam of light rays to project a primary image on a main surface, a lens system to simultaneously produce a duplicate image of the primary image on a second surface beamed in a direction different from that of the primary image and which includes a hollow tubular member mounted to the projector and including a first and a second spaced plane mirror oriented with respect to one another to project a secondary beam through the member and wherein the first plane mirror is oriented in the peripheral zone of the path of the main beam of light from the projector.

15 Claims, 2 Drawing Figures

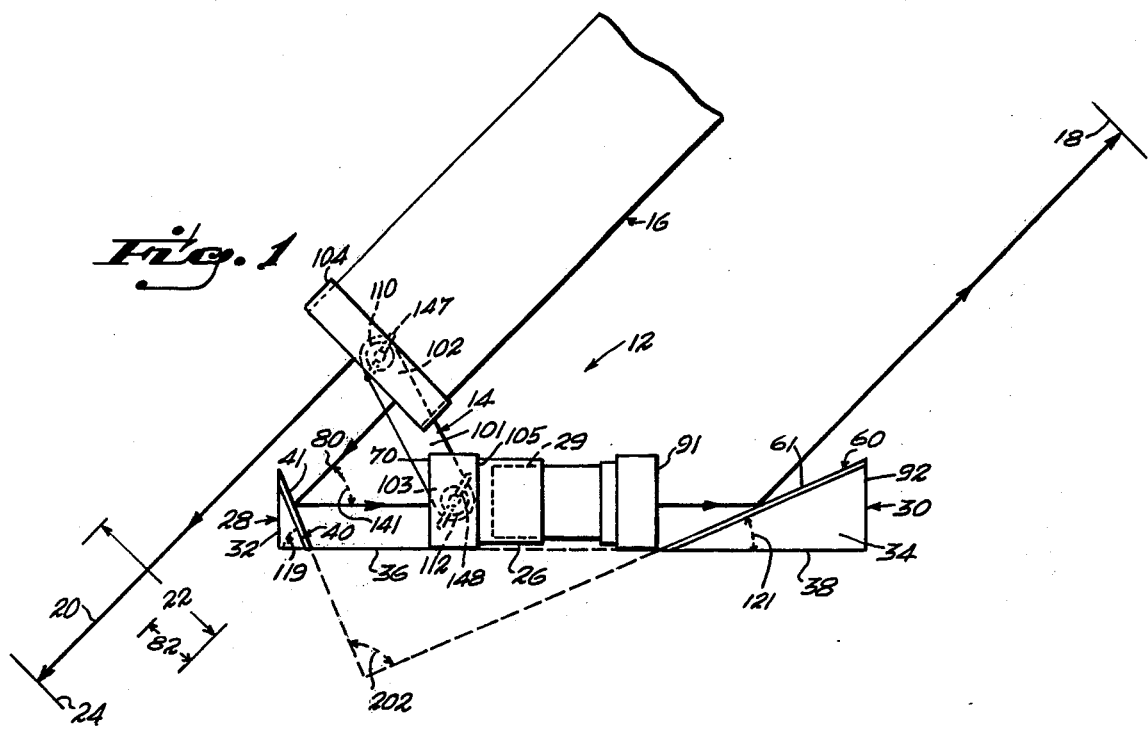
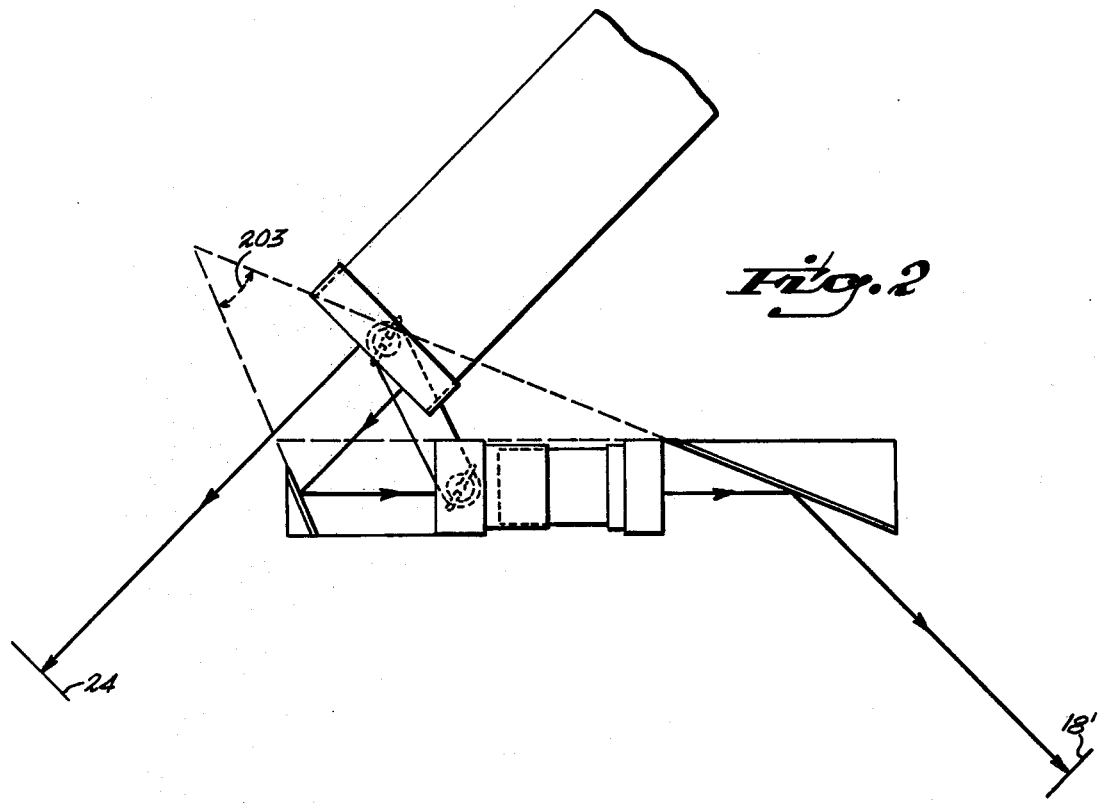

SECONDARY IMAGE REPRODUCTION DEVICE

FIELD OF THE INVENTION

This invention relates to optical devices in general and, in particular, is of a device to attach to a projector to cause a duplicate image of the primary projector image to appear on a surface which is behind the projector or, at right angles to the main projector beam. At any event, the duplicate image is an exact replica of the primary image, is reduced in size preferably, and is caused to appear at a convenient location.

BACKGROUND OF THE INVENTION

Persons operating projectors, especially optometrists and ophthalmologists find it is necessary to face the patient while the patient looks straight ahead, over the operator's shoulder, at a primary image caused by a projector. This is so that the operator can adjust the lenses of the patient until the patient is able to see the primary image clearly. Such work is rather difficult because, in the past, the operator would frequently have to turn around in order to check and see the correctness of the image as reported to him by the patient. This invention is of a device which is adapted to be attached to the projector and which taps a portion of the main projector beam and reflects it onto a surface in a convenient line of sight directly in front of the operator or to his right or left side, with the result that he does not have to continually turn his head to check to see if the patient has read the projected image correctly.

This device embodies a principle expressed by James P. C. Southall in his text "Mirrors, Prisms, and Lenses," to the effect that "if a ray lying in a principal section is reflected successively at two plane mirrors, it will be deviated from its original direction by an angle equal to twice the dihedral angle between the mirrors." The device further utilizes a principle disclosed in U.S. Pat. No. 3,768,891, wherein a duplicate image of a main projected image can be caused by positioning a mirror in the peripheral zone of the main beam and reflecting the same by that mirror and another mirror to cause a secondary image to appear, which is a duplicate of the original.

Accordingly, this invention has as an object the provision of an improvement comprising a device for use with an optical projector system to produce a duplicate image simultaneously with the main image caused by the projector and wherein the duplicate image is beamed in a direction which is 180 degrees from the path of the beam of light from the projector causing the main image or, alternatively, at an angle of 90 degrees with respect to that path and wherein the operator may, at his option, select the surface upon which the secondary or duplicate image will be beamed, all with the object of permitting an operator of a projector to face the projector, and the patient, for various adjustments of it while, at the same time, he is able to see a secondary or duplicate image in front of him or to his side which is the same as that which the patient sees and which device may be readily installed on existing projectors.

Generally speaking the optical device has as an object the provision of an improved system which may be incorporated in existing projector systems and which includes a tubular member or means, preferably with a lens system, and which includes opposite ends which are rotatable with respect to the longitudinal centerline of the tubular member and on each of which a mirror is mounted at a predetermined and selected angle so that light may enter through an opening in the tubular member and be reflected through it from a first mirror to the second mirror to be reflected upon a secondary surface causing a duplicate image.

In accordance with these general objects, this invention will now be described with reference to the accompanying drawings, in which:

DESCRIPTION OF THE DRAWINGS

FIG. 1 is a plan view of the instant invention and illustrating its use in one attitude or orientation;

FIG. 2 is a view similar to FIG. 1 and illustrating the instant invention in another attitude or orientation, as is explained more fully hereinafter.

DESCRIPTION OF THE PREFERRED EMBODIMENT

The instant invention comprises a device generally designated by the numeral 12 which is to be mounted by suitable means, such as that indicated by the numeral 14, at an angle with respect to the projector generally designated by the numeral 16. It has as a purpose to form a secondary or duplicate image on a surface generally as indicated by the numeral 18 in FIG. 1 which is directly behind the projector. This is so that an operator may face the patient while, simultaneously, he may observe in a convenient line of sight what the patient is seeing directly behind him. The instrument or device relies upon a principle set forth by James P. C. Southall in his text "Mirrors, Prisms, and Lenses," namely, that, if a ray lying in a principal section is reflected successively at two plane mirrors, it will be deviated from its original direction by an angle equal to twice the dihedral angle between the mirrors."

Referring more particularly to the drawings it is seen that the projector 16 directs a beam indicated by the numeral 20 which is generally of a cross sectional diameter indicated by the numeral 22 toward a primary surface 24 to create what can be conveniently referred to as a primary image. The projector includes a conventional lens system to focus upon the surface 24. The instant device 12 includes a hollow tubular means or member 26 with a first end zone 28 and the second end zone 30 which may be in the form of wedges 32 and 34 mounted on an axially extending portion 36 and 38 as indicated. Within the tubular member a lens system not shown, but which is conventional, is provided to focus a beam passing longitudinally therethrough, and which lens system may be regarded as being designated by the numeral 29 which permits of the preferred lens adjustment while focusing a light beam travelling through the tubular member. On the first end zone a first plane mirror 40 is provided which has a reflective surface 41 which, generally, faces toward the second end, that is, generally, axially but at a slight angle. A second plane mirror 60 is provided on the other end of the device; and this has a reflective face 61 generally facing in the direction of the first plane mirror but at a complementary angle to the longitudinal centerline of the tubular member. The means to support the mirrors are of any suitable construction, but which for purposes of this description and, for convenience only, may be in the form of wedges as described above. It will be noted that the angle of inclination of each of the mirrors is such that the total of the angles of inclination with respect to the longitudinal centerline of the hollow member is 90 degrees. The first end zone has an opening for access of light through what may be regarded as a window in the side wall of the tubular member and, in the embodiment shown in FIG. 1 this opening is the entire space between the end of the intermediate portion 70 of the tubular member and the end 28 of the device. This opening in any event is such that a line of sight through the first opening and toward the reflective surface 41 of the first plane mirror 40, that is the line of sight designated by the numeral 80 is in the peripheral zone, as indicated by the numeral 82 of the main diameter 22 of the beam of light from the projector so that the rays travelling along the line of sight 80 are reflected by the reflective surface 41 of the first mirror 40 through the tubular member and the lens system in the tubular member to be reflected by the second mirror 60 and caused to emerge through the opening between the second end 91 of the intermediate portion of the tubular member and the terminal end 92 to impinge upon a second surface 18.

In this manner, when the device is mounted as shown in FIG. 1, light will be reflected on the surface 18 which will be a duplicate of the image seen on the surface 24. The device previously described is mounted to the projector at a suitable angle such that the situation described above exists, which may be accomplished by relative adjustment of the device with respect to the centerline of the projected beam.

In the preferred embodiment the means to mount includes an arm 101 with a first end 102 and a second end 103 and means on the first end and the second end, such as a band 104 and 105 sized to be received about the projector and the diameter of the device respectively. Preferably pivot means are provided, such as that designated by the numeral 110 and that designated by the numeral 112 for swinging movement about either of parallel pivot axis for alignment of the device generally by swinging movement about the pivot 110 and adjustment of the device on the end of the arm about the pivot 112.

In the preferred embodiment, the angle of inclination indicated by the arrowed line 119 is 67½ degrees and that indicated by the arrowed line 121 is 22½ degrees, totalling to 90 degrees, in which event the angle indicated by the line 141 is 45 degrees. When in this particular orientation through the means to mount, the reflected duplicate image will be cast 180 degrees with respect to the projection path of the main beam of emergent light causing the duplicate image upon the surface 18. The device once in position may be adjusted by a suitable lock screw 147 and 148 serving as keeper means. Referring to FIG. 2, which illustrates the same device, it is seen that the first end is in the same position as is described with reference to FIG. 1; however, the second end has been rotated about the longitudinal axis of the device through 180 degrees with the result that the angle of reflection from the second mirror is such that the duplicate image is cast upon the surface 18'. It will be noted that in this orientation the surface 18' is parallel to the beam of emergent light but spaced from it so that the operator may look to the side and not have to turn all the way around to look in the direction in which the patient is looking.

It should further be noted that the angle indicated by the numeral 202 in FIG. 1, that is the angle between the dotted lines is 90 degrees. In other words, the planes of the respective plane mirrors intersect at an angle of 90 degrees. When rotated to the attitude shown in FIG. 2, the included angle between the planes of the mirrors is 45 degrees, see the arrowed line 203. There has thus been described a preferred embodiment of a device which may be attached to a projector which will cause a duplicate image to appear and may be viewed by the operator by looking 180 degrees away from the direction in which a patient is looking or, optionally, to the side.

What is claimed is:

1. For attachment to a projector having a beam opening for passage of a primary beam of emergent light rays to project a primary image on a main surface and wherein the projector includes a main lens system;
   a device to simultaneously produce a duplicate image of the primary image on a second surface, said device comprising:
   a member including a first end zone portion and a second end zone portion and an intermediate portion between the end zone portions, and said member having a longitudinal axis through the portions and defining a secondary light beam path,
   a first plane mirror having a reflective surface on the first end zone with the reflective surface facing toward said second end zone and at a first angle with respect to the longitudinal axis of the member;
   a second plane mirror having a reflective face on the second end zone with the reflective surface facing toward said first end zone and at a second angle with respect to the longitudinal axis of the member,
   the sum of said first and said second angles being substantially 90 degrees,
   said first end zone having an opening between the intermediate portion and the first plane mirror such that a line of sight through said first opening and toward the reflective surface of said first plane mirror reflects light rays entering the first opening which impinge upon the first plane mirror parallel to said axis along said secondary light beam path towards the second plane mirror; and
   said second end zone having an opening between the intermediate portion and the second plane mirror so that light rays traveling along the light beam path are reflected through said second opening,
   means to mount the device to a projector oriented so that (a) the first plane mirror and (b) the first opening in the first end zone are in the peripheral portion of the primary beam of emergent light rays projecting the primary image on the main surface to reflect a portion of said primary beam from the first mirror parallel to the axis of the member to be reflected by the second mirror to simultaneously project and produce a secondary image on a second surface which is a duplication of the primary image;
   an auxiliary lens means in the path on the intermediate portion with a lens axis parallel to the axis of the member to focus the light rays reflected from the first mirror to the second mirror on the second surface; and
   means connecting the second end zone portion to the intermediate portion including adjustment means to rotate the second mirror about the axis of the member and relative to the first mirror through 180 degrees of rotation.

2. The device as set forth in claim 1 wherein said first angle is 22½ degrees and said second angle is 67½ degrees.

3. The device as set forth in claim 1 wherein said first end zone and said second end zone are rotatably connected to said intermediate portion for rotation of said first plane mirror and said second mirror respectively about the longitudinal axis of said tubular member.

4. The device as set forth in claim 3 wherein said first angle is 22½ degrees and said second angle is 67½ degrees.

5. The device as set forth in claim 1 wherein the means to mount the member to a projector includes an arm having a first end and a second end and means to connect are provided on the second end of the arm to connect the arm to the member and on the first end of the arm to connect the arm to a projector.

6. The device as set forth in claim 5 wherein the means to connect the second end of the arm includes pivot means for swinging movement of adjustment of the member on the end of the arm.

7. The device as set forth in claim 6 wherein the means to connect includes pivot pin means on the first end of the arm for swinging movement of adjustment of the device relative to the projector.

8. The device as set forth in claim 1 wherein the plane of said first mirror and the plane of said second mirror intersect at an angle of 90 degrees.

9. The device as set forth in claim 1 wherein the plane of said first mirror and the plane of said second mirror intersect one another at an included angle of 45 degrees.

10. The device as set forth in claim 9 wherein said first end zone and said second end zone are rotatably connected to said intermediate portion for rotation of said first plane mirror and said second plane mirror relative to one another about the longitudinal axis of said member.

11. The device as set forth in claim 6 wherein lock means are provided to keep the member in a predetermined position of adjustment.

12. The device as set forth in claim 7 wherein keeper means are provided to maintain the relative position of the device relative to the projector.

13. The device as set forth in claim 3 wherein the means to mount the member to a projector includes an arm having a first end and a second end and means to connect are provided on the second end of the arm to connect the arm to the member and on the first end of the arm to connect the arm to a projector.

14. The device as set forth in claim 13 wherein the means to connect the second end of the arm includes pivot means for swinging movement of adjustment of the member on the end of the arm.

15. In combination, (A) a projector having a beam opening for passage of a primary beam of emergent light rays to project a primary image on a main surface and wherein the projector includes a main lens system; and (B) a device to simultaneous produce a duplicate image of the primary image on a second surface, said device having a first end zone portion and a second end zone portion and an intermediate portion between the end zone portions and defining a secondary light beam path, a first plane mirror having a relective surface on the first end zone with the reflective surface facing toward said second end zone and at a first angle with respect to the secondary light beam path, a second plane mirror having a reflective surface on the second end zone with the reflective surface facing toward said first end zone and at a second angle with respect to the secondary light beam path, the sum of said first and said second angles being substantially 90 degrees, said first end zone being open between the intermediate portion and the first plane mirror such that a line of sight through said first opening and toward the reflective surface of said first plane mirror reflects light rays entering the first opening which impinge upon the first plane mirror parallel and along said secondary light beam path towards the second plane mirror; and said second end zone being open between the intermediate portion and the second plane mirror so that light rays traveling along the secondary light beam path are reflected from said open second end zone, said device being arranged relative to the primary light beam (a) with the secondary light beam path at an angle of 45 degrees, and (b) with the first plane mirror and the first opening in the first end zone in the peripheral portion of the primary beam of emergent light rays projecting the primary image on the main surface, to reflect a portion of said primary beam from the first mirror along the secondary light beam path to be reflected by the second mirror to simultaneously project and produce a secondary image on a second surface which is a duplication of the primary image; a lens means in perpendicular relation spanning the secondary light beam path to focus the light rays reflected from the first mirror to the second mirror on the second surface; and adjustment means to rotate the second mirror about the axis of the member and relative to the first mirror through 180 degrees of rotation.

* * * * *